(12) United States Patent
Puentener et al.

(10) Patent No.: US 7,262,303 B2
(45) Date of Patent: Aug. 28, 2007

(54) PROCESS FOR THE PRODUCTION OF CHIRAL PROPIONIC ACID DERIVATIVES

(75) Inventors: Kurt Puentener, Basel (CH); Michelangelo Scalone, Birsfelden (CH)

(73) Assignee: Hoffman-La Roche Inc., Nutley, NJ (US)

( * ) Notice: Subject to any disclaimer, the term of this patent is extended or adjusted under 35 U.S.C. 154(b) by 544 days.

(21) Appl. No.: 10/933,176

(22) Filed: Sep. 2, 2004

(65) Prior Publication Data

US 2005/0070714 A1    Mar. 31, 2005

(30) Foreign Application Priority Data

Sep. 29, 2003  (EP)  ................... 03021700

(51) Int. Cl.
*C07D 263/32*   (2006.01)
(52) U.S. Cl. ........................................ 548/235
(58) Field of Classification Search ................. 548/235
See application file for complete search history.

(56) References Cited

U.S. PATENT DOCUMENTS 6,642,389 B2 * 11/2003 Binggeli et al. ............ 548/236

FOREIGN PATENT DOCUMENTS

WO    WO 00/66572 A1    11/2000
WO    WO 02/092084      11/2002

OTHER PUBLICATIONS

Schmidt, U., et al., Synthesis and Enantioselective Hydrogenation of alpha-Acyloxyacrylates, Synthesis, Georg Thieme Verlag Stuttgart, DE, vol. 13, 1994, pp. 1138-1140, XP001204845.
Burk, M.J., et al, Rh-DuPHOS-Catalzed Enantioselective Hydrogenation of Enol Esters, Application to the Synthesis of Highly Enantioenriched alpha-Hydroxy Esters and 1,2-Diols, Journal of the American Chemical Society, Washing, DC, US, vol., 120, No. 18, 1998, pp. 4345-4353, XP002315073.

* cited by examiner

*Primary Examiner*—Kamal A. Saeed
(74) *Attorney, Agent, or Firm*—George W. Johnston; Dennis P. Tramaloni; Brian C. Remy

(57) ABSTRACT

The present invention is concerned with a novel process for the preparation of compounds of formula I

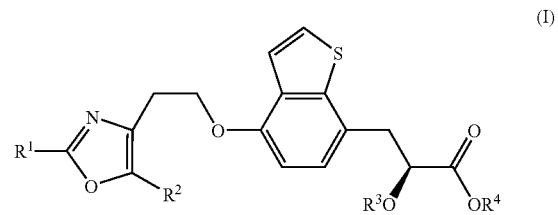

comprising catalytic asymmetric hydrogenation of a compound of formula (II)

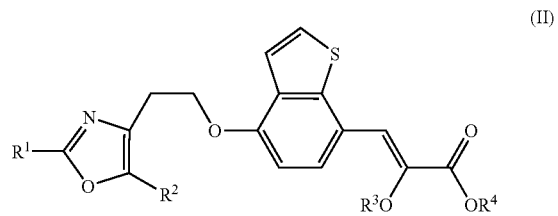

in the presence of a catalyst comprising ruthenium and a chiral diphosphine ligand or comprising rhodium and a chiral diphosphine ligand, wherein $R^1$, $R^2$, $R^3$ and $R^4$ are as defined in the specification and claims. The compounds of formula I and the corresponding salts and/or esters are pharmaceutically active substances.

21 Claims, No Drawings

PROCESS FOR THE PRODUCTION OF CHIRAL PROPIONIC ACID DERIVATIVES

FIELD OF THE INVENTION

The present invention is concerned with a novel process for the preparation of chiral propionic acid derivatives, especially with the preparation of (S)-2-methoxy-3-{4-[2-(5-methyl-2-phenyl-oxazol-4-yl)-ethoxy]-benzo[b]thiophen-7-yl}-propionic acid. (S)-2-methoxy-3-{4-[2-(5-methyl-2-phenyl-oxazol-4-yl)-ethoxy]-benzo[b]thiophen-7-yl}-propionic acid and its salts are pharmaceutically active compounds. These compounds are known in the art and are described for example in International Patent Application WO 02/092084. They are especially useful for the prophylaxis and/or treatment of diabetes mellitus type I and II.

BACKGROUND OF THE INVENTION

Methods for the preparation of (S)-2-methoxy-3-{4-[2-(5-methyl-2-phenyl-oxazol-4-yl)-ethoxy]-benzo[b]thiophen-7-yl}-propionic acid have been described in WO 02/092084. However, these methods include a large number of individual and costly process steps and exhibit a low yield. These methods known in the art are consequently unsuitable for the commercial large scale production of (S)-2-methoxy-3-{4-[2-(5-methyl-2-phenyl-oxazol-4-yl)-ethoxy]-benzo[b]thiophen-7-yl}-propionic acid.

It has surprisingly been found that using the process according to the present invention (S)-2-methoxy-3-{4-[2-(5-methyl-2-phenyl-oxazol-4-yl)-ethoxy]-benzo[b]thiophen-7-yl}-propionic acid can be prepared much more economically, with less process steps under moderate conditions with an outstanding yield. Further, crude intermediate products can mostly be used in subsequent reaction steps without the need of any additional purification steps.

SUMMARY OF THE INVENTION

The present invention refers to a process for the preparation of compounds of formula (I)

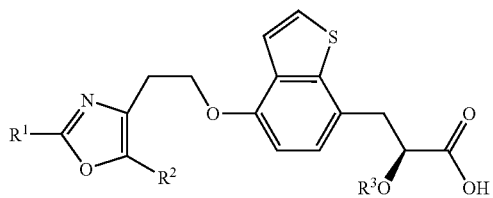

or salts thereof, comprising catalytic asymmetric hydrogenation of a compound of formula (II)

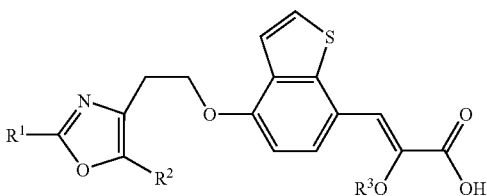

or salts thereof, in the presence of a catalyst comprising ruthenium and a chiral diphosphine ligand or comprising rhodium and a chiral diphosphine ligand, to yield said compound of formula (I), wherein $R^1$ is aryl or heteroaryl, $R^2$ is lower-alkyl, $R^3$ is lower-alkyl.

Unless otherwise indicated the following definitions are set forth to illustrate and define the meaning and scope of the various terms used to describe the invention herein.

The term "halogen" refers to fluorine, chlorine, bromine and iodine. The term "halogenide" refers to a negatively charged halogen anion.

In this specification the term "lower" is used to mean a group consisting of one to seven, preferably of one to four carbon atom(s).

The term "alkyl" refers to a branched or straight chain monovalent saturated aliphatic hydrocarbon radical of one to twenty carbon atoms, preferably one to sixteen carbon atoms. Lower-alkyl groups as defined below are preferred alkyl groups.

The term "lower-alkyl" refers to a branched or straight chain monovalent alkyl radical of one to seven carbon atoms, preferably one to four carbon atoms. This term is further exemplified by such radicals as methyl, ethyl, n-propyl, isopropyl, i-butyl, n-butyl, t-butyl and the like with methyl and ethyl being preferred.

The term "alkoxy" refers to the group alkyl-O—, the term "lower alkoxy" to the group lower-alkyl-O—.

The term "cycloalkyl" refers to a monovalent carbocyclic radical of 3 to 10 carbon atoms, preferably 3 to 6 carbon atoms, such as cyclopropyl, cyclobutyl, cyclopentyl, or cyclohexyl.

The term "aryl" relates to the phenyl or naphthyl group, preferably the phenyl group, which can optionally be mono- or multiply-substituted, particularly mono-, di- or tri-substituted by halogen, hydroxy, CN, $CF_3$, $NO_2$, $NH_2$, $N(H, lower-alkyl)$, $N(lower-alkyl)_2$, carboxy, aminocarbonyl, lower-alkyl, lower-alkoxy, phenyl and/or phenyloxy. Preferred substituents are halogen, lower-alkyl, and/or lower-alkoxy, particularly lower-alkyl and/or lower-alkoxy.

The term "heteroaryl" refers to an aromatic 5- or 6-membered ring which can comprise 1, 2 or 3 atoms selected from nitrogen, oxygen and/or sulphur such as furyl, pyridyl, 1,2-, 1,3- and 1,4-diazinyl, thienyl, isoxazolyl, oxazolyl, imidazolyl, or pyrrolyl. The term "heteroaryl" further refers to bicyclic aromatic groups comprising two 5- or 6-membered rings, in which one or both rings can comprise 1, 2 or 3 atoms selected from nitrogen, oxygen or sulphur such as e.g. indole or quinoline, or partially hydrogenated bicyclic aromatic groups such as e.g. indolinyl. A heteroaryl group may have a substitution pattern as described earlier in connection with the term "aryl". Preferred heteroaryl groups are thienyl and furyl.

The term "pharmaceutically acceptable salts" embraces salts of the compounds of formula (I) with pharmaceutically acceptable bases such as alkali salts, e.g. Na- and K-salts, alkaline earth salts, e.g. Ca- and Mg-salts, and ammonium or lower-alkyl-substituted ammonium salts, such as e.g. trimethylammonium salts.

DETAILED DESCRIPTION OF THE INVENTION

In detail, the present invention refers to a process for the preparation of compounds of formula (I)

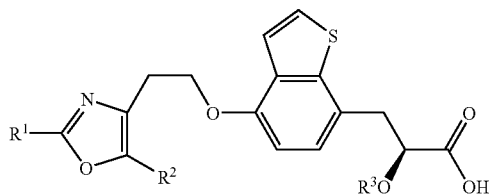

(I)

or salts thereof, comprising catalytic asymmetric hydrogenation of a compound of formula (II)

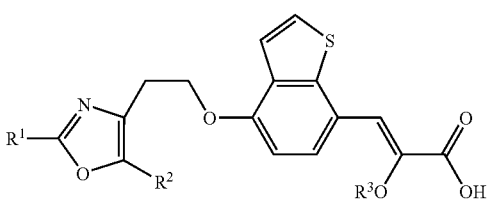

(II)

or salts thereof, in the presence of a catalyst comprising ruthenium and a chiral diphosphine ligand or comprising rhodium and a chiral diphosphine ligand, to yield said compound of formula (I), wherein $R^1$ is aryl or heteroaryl, $R^2$ is lower-alkyl, $R^3$ is lower-alkyl.

The catalysts mentioned above are complexes of ruthenium or rhodium respectively with a chiral diphosphine ligand. In such ruthenium complexes, ruthenium is characterised by the oxidation number II. Such ruthenium complexes can optionally comprise further ligands, either neutral or anionic. Examples of such neutral ligands are e.g. olefines, e.g. ethylene, propylene, cyclooctene, 1,3-hexadiene, norbornadiene, 1,5-cyclooctadiene, benzene, hexamethylbenzene, 1,3,5-trimethylbenzene, p-cymene, or also solvents such as e.g. tetrahydrofuran, dimethylformamide, acetonitrile, benzonitrile, acetone and methanol.

Examples of such anionic ligands are $CH_3COO^-$, $CF_3COO^-$ or halogenides. If the ruthenium complex is charged, non coordinating anions such as halogenides, $BF_4^-$, $ClO_4^-$, $SbF_6^-$, $PF_6^-$, $B(phenyl)_4^-$, $B(3,5\text{-di-trifluoromethyl-phenyl})_4^-$, $CF_3SO_3^-$, $C_6H_5SO_3^-$ are present Preferred catalysts comprising ruthenium and a chiral diphosphine are of the formula [Ru(chiral diphosphine)$B_2$], wherein B is $CH_3COO^-$, $CF_3COO^-$ or a halogenide.

In the rhodium complexes referred to above, rhodium is characterised by the oxidation number I. Such rhodium complexes can optionally comprise further ligands, either neutral or anionic. Examples of such neutral ligands are e.g. olefines, e.g. ethylene, propylene, cyclooctene, 1,3-hexadiene, norbornadiene, 1,5-cyclooctadiene (COD), benzene, hexamethylbenzene, 1,3,5-trimethylbenzene, p-cymene, or also solvents such as e.g. tetrahydrofuran, dimethylformamide, acetonitrile, benzonitrile, acetone and methanol. Example of such anionic ligands are halogenides, $CH_3COO^-$ or $CF_3COO^-$. If the rhodium complex is charged, non coordinating anions such as a halogenide, $BF_4^-$, $ClO_4^-$, $SbF_6^-$, $PF_6^-$, $B(phenyl)_4^-$, $B(3,5\text{-di-trifluoromethyl-phenyl})_4^-$, $CF_3SO_3^-$, $C_6H_5SO_3^-$ are present. Preferred catalysts comprising rhodium and a chiral diphosphine are of the formula [Rh(chiral diphosphine)L]B, wherein B is $BF_4^-$, $ClO_4^-$, $SbF_6^-$, $PF_6^-$, $B(phenyl)_4^-$, $B(3,5\text{-di-trifluoromethyl-phenyl})_4^-$, $CF_3SO_3^-$, or $C_6H_5SO_3$, and L is 1,5-cyclooctadiene, 2 ethylene, 2 propylene, 2 cyclooctene, 1,3-hexadiene, norbornadiene. If L is a ligand comprising 2 double bonds, e.g. 1,5-cyclooctadiene, only 1 such L is present. If L is a ligand comprising only 1 double bond, e.g. ethylene, 2 such L are present present As salts of the compounds of formula (I) and (II) respectively come into consideration alkaline salts, e.g. K or Na, earth alkaline salts, e.g. Mg or Ca, and ammonium or lower-alkyl-substituted ammonium salts such, as e.g. trimethylammonium salts. A process as described above, which refers to the compounds of formula (I) and (II) respectively, not the salts, is preferred.

In a preferred embodiment of the present invention, the chiral diphosphine ligand is characterised by formula (III), (IV), (V), (VI) or (VII)

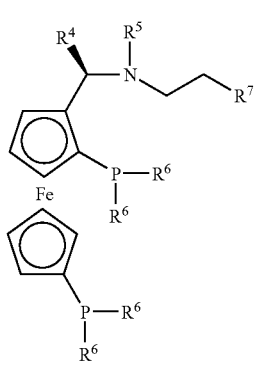

(III)

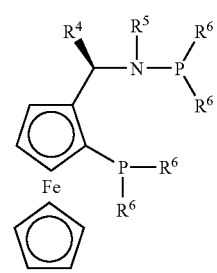

(IV)

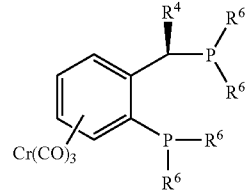

(V)

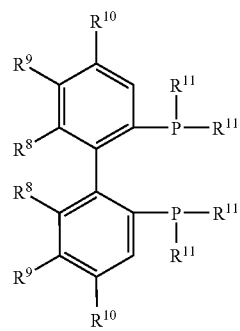

(VI)

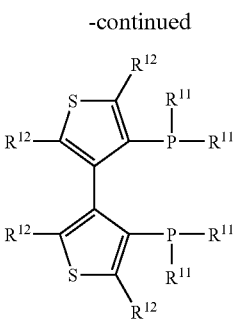

(VII)

wherein

R⁴ is lower-alkyl;

R⁵ is lower-alkyl;

R⁶ independently is aryl, heteroaryl, cylcoalkyl or lower-alkyl;

R⁷ is N(lower-alkyl)₂ or piperidinyl;

R⁸ is lower-alkyl, lower-alkoxy, hydroxy or lower-alkyl-C(O)O—;

R⁹ and R¹⁰ independently are hydrogen, lower-alkyl, lower-alkoxy or di(lower-alkyl)amino; or R⁸ and R⁹ or R⁹ and R¹⁰ which are attached to the same phenyl group, or both R⁸ attached to different phenyl groups, taken together, are —X—(CH₂)ₙ—Y—, wherein X is —O— or —C(O)O—, Y is —O— or —N(lower-alkyl)- and n is an integer from 1 to 6; or R⁸ and R⁹, or R⁹ and R¹⁰, together with the carbon atoms to which they are attached, form a naphthyl, tetrahydronaphthyl or dibenzofuran ring;

R¹¹ independently is phenyl or napthyl, substituted with 0 to 7 substituents independently selected from the group consisting of lower-alkyl, lower-alkoxy, di(lower-alkyl)amino, morpholino, phenyl and tri(lower-alkyl)silyl;

R¹² independently is lower-alkyl.

If R¹¹ is phenyl, it is substituted with 0 to 5, preferably 0 to 3 substituents as described above.

In a more preferred embodiment, the catalyst is of the formula [Ru(chiral diphosphine)B₂], wherein the chiral diphosphine is characterised by formula (VI) or (VII) as defined in claim 2 and wherein B is CH₃COO⁻, CF₃COO⁻ or a halogenide.

Preferably, the chiral diphosphine is selected from the group consisting of: (S)-MeOBIPHEP, (S)-BIPHEMP, (S)-TMBTP, (S)-(2-Naphthyl)-MeOBIPHEP, (S)-(6-MeO-2-Naphthyl)-MeOBIPHEP, (S)-TriMeOBIPHEP, (R,R,S,S)-Mandyphos, (S)-BnOBIPHEP, (S)-BenzoylBIPHEP, (S)-pTol-BIPHEMP, (S)-tButylCOOBIPHEP, (S)-iPrOBIPHEP, (S)-pPhenyl-MeOBIPHEP, (S)-pAn-MeOBIPHEP, pTol-MeOBIPHEP, (S)-3,5-Xyl-MeOBIPHEP, (S)-3,5-Xyl-BIPHEMP, (S)-BINAP and (S)-2-Furyl-MeOBIPHEP. More preferably, the chiral diphosphine is (S)-TMBTP, (S)-(2-Naphthyl)-MeOBIPHEP or (S)-(6-MeO-2-Naphthyl)-MeOBIPHEP. Each of these chiral diphosphines individually constitutes a preferred embodiment of the present invention.

Atropisomeric diphosphines, particularly atropisomeric bi-aryl diphosphines are preferred. In atropisomers, optical activity is caused by the fact that rotation about a single bond is prevented or greatly slowed. (Lit.: J. March "Advanced Organic Chemistry", Wiley interscience, 4th edition, 1992, p. 102)).

In the catalysts described above, B preferably is CH₃COO⁻ or CF₃COO⁻. A further preferred embodiment of the present invention relates to a process as described above, wherein the catalyst is selected from the group consisting of [Ru(CH₃COO⁻)₂((S)-TMBTP)], [Ru(CF₃COO⁻)₂((S)-TMBTP)], [Ru(CH₃COO⁻)₂((S)-(2-Naphthyl)-MeOBIPHEP)], [Ru(CF₃COO⁻)₂((S)-(2-Naphthyl)-MeOBIPHEP)], [Ru(CH₃COO⁻)₂((S)-(6-MeO-2-Naphthyl)-MeOBIPHEP)] and [Ru(CF₃COO⁻)₂((S)-(6-MeO-2-Naphthyl)-MeOBIPHEP)]. Each of these catalysts individually constitute a preferred embodiment.

The process as defined above can be carried out under conditions known to the person skilled in the art. The reaction pressure is conveniently chosen in a range of e.g. 1 to 120 bar. A process as described aove, wherein the catalytic hydrogenation is carried out at a pressure of 20 to 40 bar, is preferred. The reaction temperature is conveniently chosen in the range of 0 to 120° C. A process as defined above, wherein the catalytic hydrogenation is carried out at a temperature of 20 to 60° C., is preferred.

A process as defined above, wherein the catalytic hydrogenation is carried out in the presence of a base, is also preferred. Conveniently, about 0.05 to 1 equivalent of base is used, preferably about 0.2 equivalents. Bases such as e.g. NaOH, KOH, (S)-phenylethyl-amine, Et₃N, or NaHPO₄ come into consideration. (S)-phenylethylamine is preferred.

The process of the present invention can conveniently be carried out in a solvent. A process as defined above, wherein the catalytic hydrogenation is carried out in a solvent which is methanol, dichloromethan, ethanol, tetrahydrofuran, ethylacetat or toluene, or a combination thereof, is also preferred. More preferably, the catalytic hydrogenation is carried out in a solvent which is a 3:2 mixture of methanol and dichloromethan.

Preferably, the process as defined above additionally comprises crystallisation of the compound of formula (I). More preferably, the process as defined above additionally comprising crystallisation of the compound of formula (I) as a salt with a primary amine.

Preferably, the primary amine is (S)-phenylethylamine.

The (S)-phenylethylamine salt of (S)-2-methoxy-3-{4-[2-(5-methyl-2-phenyl-oxazol-4-yl)-ethoxy]-benzo[b]thiophen-7-yl}-propionic acid can conveniently be prepared by analogous methods well known in the art, e.g. by dropwise addtiton of a solution of is (S)-phenylethylamine in THF to a solution of S)-2-methoxy-3-{4-[2-(5-methyl-2-phenyl-oxazol-4-yl)-ethoxy]-benzo[b]thiophen-7-yl}-propionic acid in THF at e.g. 63-65° C. Subsequent addition of seed crystals cause the immediate start of the crystallization.

In a preferred process as defined above, the compound of formula (I) is (S)-2-methoxy-3-{4-[2-(5-methyl-2-phenyl-oxazol-4-yl)-ethoxy]-benzo[b]thiophen-7-yl}-propionic acid.

If desired, compounds of formula I can be converted to a corresponding salt, e.g. the sodium or potassium salt. Such a conversion may be carried out under basic conditions, e.g. with NaOH or KOH in THF. In a preferred embodiment, a process as defined above additionally comprises the conversion of the compound of formula (I) into a pharmaceutically acceptable salt. One embodiment of the above described process additionally comprises the conversion of a compound of formula I to the corresponding sodium salt.

A process as defined above, wherein $R^1$ is aryl, particularly phenyl, is preferred. In another preferred embodiment $R^2$ is methyl. A further preferred embodiment relates to a process as defined above, wherein $R^3$ is methyl.

A particularly preferred embodiment relates to a process as defined above for the preparation of (S)-2-methoxy-3-{4-[2-(5-methyl-2-phenyl-oxazol-4-yl)-ethoxy]-benzo[b]thiophen-7-yl}-propionic acid, comprising a) reacting 4-[2-(5-methyl-2-phenyl-oxazol-4-yl)-ethoxy]-benzo[b]thiophen-7-carbaldehyde with methoxyacetic acid methyl ester to yield 3-hydroxy-2-methoxy-3-{4-[2-(5-methyl-2-phenyl-oxazol-4-yl)-ethoxy]-benzo[b]thiophen-7-yl}-propionic acid methyl ester;

b) converting 3-hydroxy-2-methoxy-3-{4-[2-(5-methyl-2-phenyl-oxazol-4-yl)-ethoxy]-benzo[b]thiophen-7-yl}-propionic acid to (Z)-2-methoxy-3-{4-[2-(5-methyl-2-phenyl-oxazol-4-yl)-ethoxy]-benzo[b]thiophen-7-yl}-acrylic acid methyl ester.

c) converting (Z)-2-methoxy-3-{4-[2-(5-methyl-2-phenyl-oxazol-4-yl)-ethoxy]-benzo[b]thiophen-7-yl}-acrylic acid methyl ester to (Z)-2-methoxy-3-{4-[2-(5-methyl-2-phenyl-oxazol-4-yl)-ethoxy]-benzo[b]thiophen-7-yl}-acrylic acid.

d) hydrogenating (Z)-2-methoxy-3-{4-[2-(5-methyl-2-phenyl-oxazol-4-yl)-ethoxy]-benzo[b]thiophen-7-yl}-acrylic acid using a procedure as defined above to yield (S)-2-methoxy-3-{4-[2-(5-methyl-2-phenyl-oxazol-4-yl)-ethoxy]-benzo[b]thiophen-7-yl}-propionic acid.

Step a) of the process defined above is an aldol reaction and can e.g. be performed with strong base such as e.g. LDA in a mixture of dichloromethane and THF at a temperature of e.g. −78° C.

Step b) of the process described above is conveniently carried out with sulfuric acid in a solvent such as e.g. DMF at a temperature of e.g. 100° C.

Step c) of the process described above is a saponification and can e.g. be performed in a mixture of an aqueous strong base such as e.g. KOH and methanol at a temperature of e.g. 60° C.

The invention further comprises the use of any of the above described processes for the preparation of (S)-2-methoxy-3-{4-[2-(5-methyl-2-phenyl-oxazol-4-yl)-ethoxy]-benzo[b]thiophen-7-yl}-propionic acid.

A further embodiment of the present invention comprises the compound (Z)-2-Methoxy-3-{4-[2-(5-methyl-2-phenyl-oxazol-4-yl)-ethoxy]-benzo[b]thiophen-7-yl}-acrylic acid methyl ester. This compound is an intermediate product or educt respectively of the processes described above Scheme 1 summarizes one possible embodiment of the above described process and the reaction conditions for the individual reaction steps.

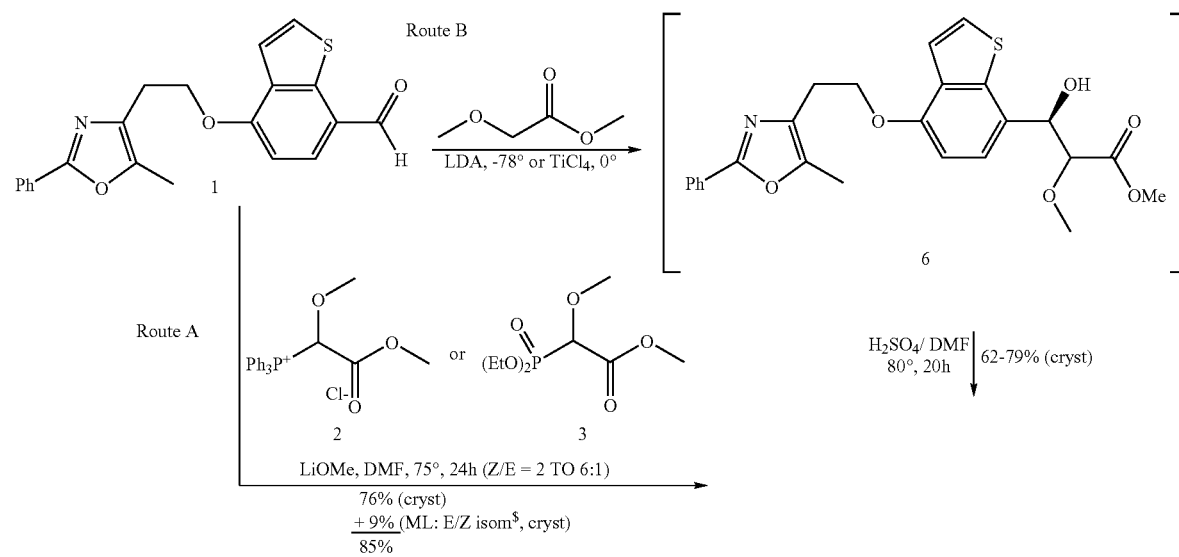

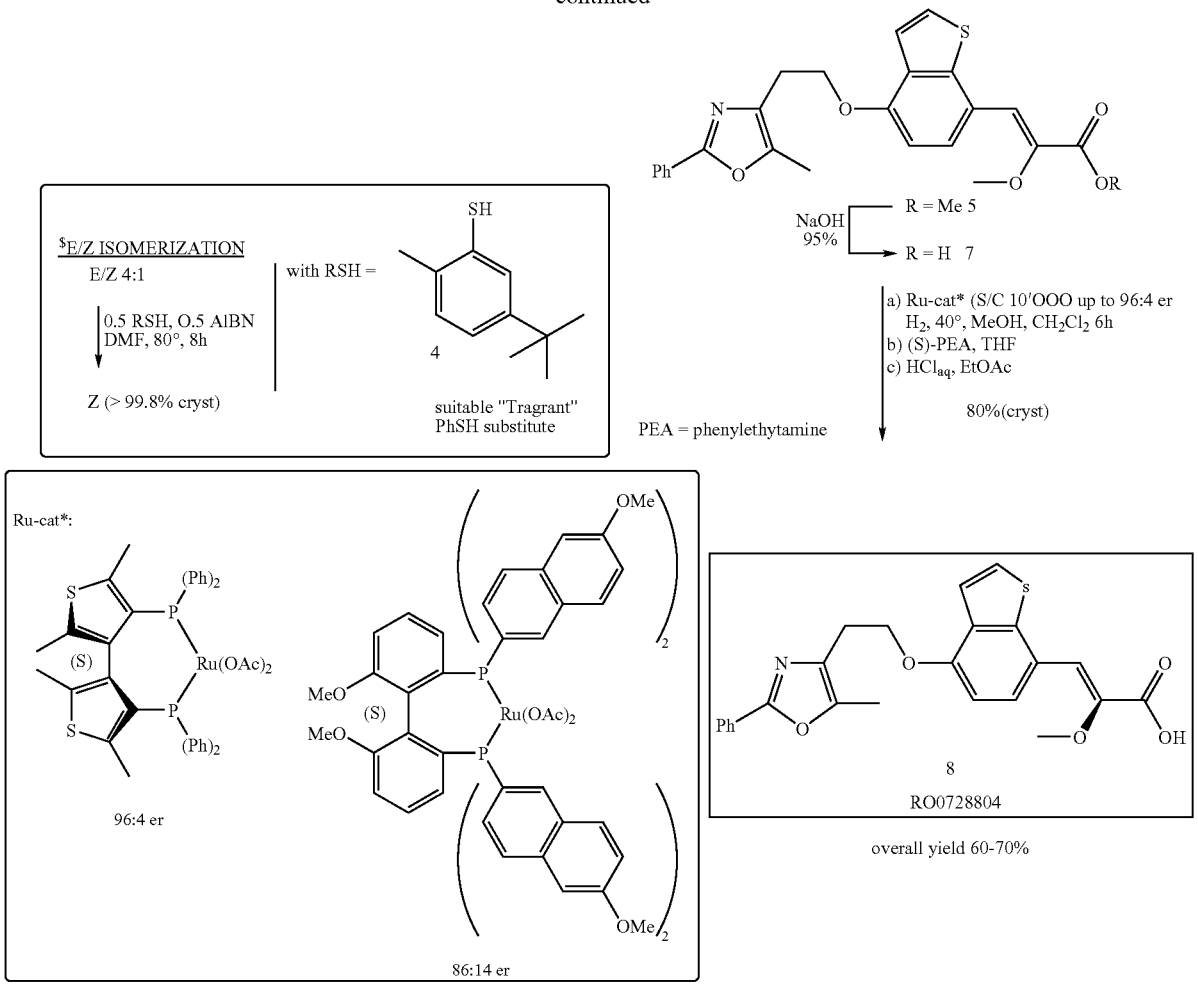

The reaction conditions for the above reactions can vary to a certain extent. Methods to perform the above described reactions and processes are known in the art or can be deduced in analogy from the examples. Starting materials are commercially available or can be made by methods analogous to those described in the example.

The following examples shall illustrate preferred embodiments of the present invention but are not intended to limit the scope of the invention.

EXAMPLES

Abbreviations

DMF=dimethylformamide, LDA=lithiumdiisopropylamide, r.t.=room temperature, THF=tetrahydrofurane, TFA=trifluoroacetate.

| Acronyms of diphosphine ligands | |
|---|---|
| MeOBIPHEP | (6,6'-Dimethoxybiphenyl-2,2'-diyl)bis(diphenylphosphin) |
| BIPHEMP | (6,6'-Dimethylbiphenyl-2,2'-diyl)bis(diphenylphosphin) |
| TMBTP | 2,2',5,5'-Tetramethyl-4,4'-bis(diphenylphosphino)-3,3'-bithiophene |
| (2-Naphthyl)-MeOBIPHEP | (6,6'-Dimethoxybiphenyl-2,2'-diyl)bis(di-2-naphthyl-phosphin) |
| (6-MeO-2-Naphthyl)-MeOBIPHEP | (6,6'-Dimethoxybiphenyl-2,2'-diyl)bis(di-2-(6-methoxy)-naphthylphosphin) |
| TriMeOBIPHEP | Phosphine, (4,4',5,5',6,6'-hexamethoxy[1,1'-biphenyl]-2,2'-diyl)bis[diphenyl] |
| Mandyphos | 1,1'-bis[(dimethylamino)phenylmethyl]-2,2'-bis(diphenyldiphosphino)-ferrocene commercially available from OMG Hanau, Germany, catalogue nr. 68.1864.7001 |

-continued

| Acronyms of diphosphine ligands | |
|---|---|
| BnOBIPHEP | (6,6'-Dibenzyloxybiphenyl-2,2'-diyl)bis(diphenylphosphin) |
| BenzoylBIPHEP | (6,6'-Dibenzoyloxybiphenyl-2,2'-diyl)bis(diphenylphosphin) |
| pTol-BIPHEMP | (6,6'-Dimethylbiphenyl-2,2'-diyl)bis(di-p-tolylphosphin) |
| tButylCOOBIPHEP | Propanoic acid, 2,2-dimethyl-,6,6'-bis(diphenylphosphino)[1,1'-biphenyl]-2,2'-diyl ester |
| iPrOBIPHEP | (6,6'-Di-2-propoxybiphenyl-2,2'-diyl)bis(diphenyl-phosphin) |
| pPhenyl-MeOBIPHEP | Phosphine, (6,6'-dimethoxy[1,1'-biphenyl]-2,2'-diyl)bis[bis([1,1'-biphenyl]-4-yl)- |
| pAn-MeOBIPHEP | Phosphine, (6,6'-dimethoxy[1,1'-biphenyl]-2,2'-diyl)bis(bis(4-methoxyphenyl)- |
| pTol-MeOBIPHEP | (6,6'-Dimethoxybiphenyl-2,2'-diyl)bis[di(p-tolyl)phosphine] |
| 3,5-Xyl-MeOBIPHEP | Phosphine, [6,6'-dimethoxy[1,1'-biphenyl]-2,2'-diyl]bis[bis(3,5-dimethylphenyl)- |
| 3,5-Xyl-BIPHEMP | Phosphine, [6,6'-dimethyl[1,1'-biphenyl]-2,2'-diyl]bis[bis(3,5-dimethylphenyl)- |
| BINAP | 2,2'-Bis(diphenylphosphino)-1,1'-binaphthyl |
| 2-Furyl-MeOBIPHEP | (6,6'-Dimethoxybiphenyl-2,2'-diyl)bis(di-2-furylphosphin) |
| (2-Furyl)-PPFA-P(Cyp)$_2$ | N-Methyl-N-dicyclopentylphosphino-1-[2-(di-2-furylphosphino)ferrocenyl]ethylamine |
| (2-Furyl)-PPFA-P(Cy)$_2$ | N-Methyl-N-dicyclohexylphosphino-1-[-2-(di-2-furylphosphino)ferrocenyl]ethylamine |
| BPPFA-EPIP | Ferrocene, 1,1'-bis(diphenylphosphino)-2-[1-[methyl[2-(1-piperidinyl)ethyl]amino]ethyl]-, [R-(R*,S*)]- |
| BPPFA-EDMA | Ferrocene, 1,1'-bis(diphenylphosphino)-2-[1-[methyl[2-dimethylamino)ethyl]amino]ethyl]-, [R-(R*,S*)]- |
| PPCr-P(tBu)$_2$ | Chromium, [bis(1,1-dimethylethyl)[-1-[(1,2,3,4,5,6-η)--2-(diphenylphosphino)-phenyl]ethyl]phosphine]tricarbonyl- |
| 3,5-tBu,4-MeO-MeOBIPHEP | Phosphine, (6,6'-dimethoxy[1,1'-biphenyl]-2,2'-diyl)bis[bis(3,5-di-tert.-butyl-4-methoxyphenyl)- |
| 2-Thienyl-MeOBIPHEP | Phosphine, [6,6'-dimethoxy[1,1'-biphenyl]-2,2'-diyl]bis[bis(2-thienyl)- |
| Me-f-KetalPhos | 1,1'-bis-[3,4-O-isopropylidene-3,4-dihydroxy-2,5-dimethylphospholanyl)]ferrocene |
| PHANEPHOS | 4,12-Bis(diphenylphosphino)[2.2]-paracyclophane commercially available from Strem Chemicals Inc. D-77672 Kehl |

Example 1

(Z)-2-Methoxy-3-{4-[2-(5-methyl-2-phenyl-oxazol-4-yl)-ethoxy]-benzo[b]thiophen-7-yl}-acrylic acid methyl ester A suspension of 6.39 g (15.9 mmol) of methyl 2-methoxy-2-(triphenylphosphonium)-acetate chloride (Prepared from methyl 2-chloro-2-methoxyacetate and triphenylphosphine, in analogy to: P. Seneci, I. Leger, M. Souchet, G. Nadler, *Tetrahedron* 1997, 53, 17097-17114), 0.68 g of lithium methylat (17.0 mmol) and 3.89 g of 4-[2-(5-methyl-2-phenyl-oxazol-4-yl)-ethoxy]-benzo[b]thiophen-7-carbaldehyde (10.6 mmol) in 40 ml of DMF was heated for 23 h at 75° C. The light brown reaction solution was cooled to 0° C., the formed white crystals were filtered off, washed with 40 ml of methanol and dried to constant weight (20° C./1 mbar/16 h) to afford 3.54 g (73%) of the title compound with a purity of 97.5% (GC area; Method: column: DB-1 (15 m*0.32 mm); injector: 270° C.; detector: 320° C.; oven 150-310° C. (4° C./min); carrier gas: $H_2$ (60 KPa). Retention times: starting material (aldehyde 1), 23.8 min; E-ester 5, 28.8 min; Z-ester 5, 30.8 min). m.p.: 165° C. MS: 450.3 $(M+H)^+$. $^1$H-NMR (CDCl$_3$): 2.40 (s, 3H); 3.08 (t, J=6.5, 2H); 3.78 (s, 3H); 3.88 (s, 3H); 4.45 (t, J=6.5, 2H); 6.86 (d, J=8.4, 1H); 7.21 (s, 1H); 7.34 (d, J=5.5, 1H); 7.38-7.45 (m, 3H); 7.49 (d, J=5.5, 1H); 7.95-8.00 (m, 2H); 8.10 (d, J=8.4, 1H).

Example 2

(Z)-2-Methoxy-3-{4-[2-(5-methyl-2-phenyl-oxazol-4-yl)-ethoxy]-benzo[b]thiophen-7-yl}-acrylic acid methyl ester A suspension of 6.57 g of methyl 2-methoxy-2-(triphenylphosphonium)acetate chloride (16.4 mmol), 2.00 g of potassium tert.-butylat (17.5 mmol) and 4.00 g of 4-[2-(5-methyl-2-phenyl-oxazol-4-yl)-ethoxy]-benzo[b]thiophen-7-carbaldehyde (10.9 mmol) in 40 ml of DMF was heated for 23 h at 75° C. The suspension was cooled to 0° C., the solid filtered off and washed with 40 ml of methanol. The filter cake was dissolved in a mixture of 150 ml of dichloromethane and 150 ml of water, the organic layer separated, dried over sodium sulfate and evaporated to dryness to afford 3.86 g (78%) of the title compound with a purity of 97.9% (GC area) as white crystals.

Example 3

(Z)-2-Methoxy-3-{4-[2-(5-methyl-2-phenyl-oxazol-4-yl)-ethoxy]-benzo[b]thiophen-7-yl}-acrylic acid methyl ester In analogy to Example 2, 2.87 g (58%) of the title compound with a purity of 95% (GC area) were isolated from 6.57 g of methyl 2-methoxy-2-(triphenylphosphonium)acetate chloride (16.4 mmol), 0.97 g of sodium methylat (17.5 mmol) and 4.00 g of 4-[2-(5-methyl-2-phenyl-oxazol-4-yl)-ethoxy]-benzo[b]thiophen-7-carbaldehyde (10.9 mmol).

Example 4

(Z)-2-Methoxy-3-{4-[2-(5-methyl-2-phenyl-oxazol-4-yl)-ethoxy]-benzo[b]thiophen-7-yl}-acrylic acid methyl ester A suspension of 81.05 g of methyl 2-methoxy-2-(triphenylphosphonium)acetate chloride (202.2 mmol), 8.62 g of lithium methylat (215.7 mmol) and 50.00 g of 4-[2-(5-methyl-2-phenyl-oxazol-4-yl)-ethoxy]-benzo[b]thiophen-7-carbaldehyde (134.8 mmol) in 500 ml of DMF was heated for 24 hours at 75°. The light brown reaction solution was cooled to 0° C., the formed crystals were filtered off and purified as described in Example 1 to yield 46.76 g (76%) of the titled compound with a purity of 97.7% (GC area). The mother liquor, which contained according to GC 5.6 area-% E-ester 5, 1.3 area-% Z-ester 5 and 87.5 area-% triphenylphosphine was treated with 3.04 g of 2-methyl-5-tert.-butylthiophenol (16.8 mmol) and 2.76 g of α,α'-azo-isobutyronitril (16.8 mmol). The resulting dark brown solution was stirred for 16 h at 90° C. Additional 6.08 g of 2-methyl-5-tert.-butylthiophenol (33.6 mmol) and 5.42 of α,α'-azo-isobutyronitril (33.6 mmol) were added, the reaction solution stirred for additional 6 h at 90° C. and then cooled to room temperature. Under stirring, 200 ml water were added and the formed suspension cooled to 0° C. The solid was filtered off, digested in 100 ml of methanol at r.t. for 15 min, filtered off and washed with 100 ml of methanol in two portions. The light brown filter cake was dried to a constant weight of 7.72 g. Crystallization from 30 ml of DMF, afforded 5.62 g (9.3%) of the title compound with a purity of 99% (GC area) as light brown crystals.

Example 5

(Z)-2-Methoxy-3-{4-[2-(5-methyl-2-phenyl-oxazol-4-yl)-ethoxy]-benzo [b]thiophen-7-yl}-acrylic acid methyl ester A suspension of 6.07 g (20.2 mmol) of (diethoxyphosphoryl)-methoxy acetic acid methyl ester (H. Gross, *Justus Liebigs Ann. Chem.* 1967, 707, 35-43), 0.86 g of lithium methylat (21.6 mmol) and 5.00 g of 4-[2-(5-methyl-2-phenyl-oxazol-4-yl)-ethoxy]-benzo[b]thiophen-7-carbaldehyde (13.5 mmol) in 50 ml of DMF was heated for 21 h at 75° C. The suspension was cooled to 0° C., the solid filtered off and washed with 30 ml of cold (−15° C.) ethanol. The filter cake was dissolved in a mixture of 100 ml dichloromethane and 60 ml of water, the organic layer separated, dried over sodium sulfate and evaporated to dryness. Thereby, 3.45 g (55%) of the title compound with a purity of 91% (GC area) were obtained as white crystals.

Example 6 a] 3-Hydroxy-2-methoxy-3-{4-[2-(5-methyl-2-phenyl-oxazol-4-yl)-ethoxy]-benzo[b]thiophen-7-yl}-propionic acid methyl ester (syn/anti mixture)

To a solution of 3.17 ml methoxyacetic acid methyl ester (31.4 mmol) in 30 ml of THF, 17 ml of LDA (2M in THF/heptane/ethylbenzene, 34.2 mmol) were added dropwise within 15 min at −78° C. After stirring for additional 15 min, a solution of 5.00 g of 4-[2-(5-methyl-2-phenyl-oxazol-4-yl)-ethoxy]-benzo[b]thiophen-7-carbaldehyde (13.7 mmol) in 70 ml of dichloromethane was added dropwise within 20 min. The dark brown reaction solution was stirred for additional 60 min, then warm up to room temperature within 150 min, cooled to 0° C. again and treated with 50 ml of ice water and 6 ml of conc. hydrochloric acid (pH 3). The organic layer was separated, washed with 25 ml water, dried over sodium sulfate and evaporated to dryness to yield 8.81 g of crude product as a brown oil. Flash chromatography ($SiO_2$, dichloromethane/AcOEt=9/1) yielded 5.89 g (91%) of the title compound as a syn/anti mixture of 1:4 with a purity of 98.3% (GC area; method: column: DB-1 (15 m*0.32 mm); injector: 270° C.; detector: 320° C.; oven 150-310° C. (4° C./); carrier gas: $H_2$ (60 KPa); samples silylated with BSTFA/pyridine. Retention times: starting material (aldehyde 1), 23.8 min; syn-alcohol 6, 28.1 min; anti-alcohol 6, 28.5 min) as a yellowish crystalline solid.

MS: 468.2 $(M+H)^+$; $^1$H-NMR ($CDCl_3$): Anti-isomer: 2.40 (s, 3H); 2.98 (d, J=4.0, 1H); 3.07 (t, J=6.6, 2H); 3.34 (s, 3H); 3.65 (s, 3H); 4.20 (d, J=5.8, 1H); 4.40 (t, J=6.6, 2H); 5.25 (dd, J=5.8, 4.0, 1H); 6.78 (d, J=8.1, 1H); 7.10-7.45 (m, 5H); 7.49 (d, J=5.6, 1H); 7.96-8.00 (m, 2H). Syn-isomer: 2.40 (s, 3H); 3.07 (t, J=6.6, 2H); 3.15-3.25 (br, 1H); 3.40 (s, 3H); 3.59 (s, 3H); 4.17 (d, J=5.8, 1H); 4.39 (t, J=6.6, 2H); 5.15 (d, J=5.8, 1H); 6.77 (d, J=8.2, 1H); 7.24 (d, J=8.2, 1H); 7.33 (d, J=5.4, 1H); 7.37-7.46 (m, 3H); 7.49 (d, J=5.4, 1H); 7.93-8.03 (m, 2H).

b] (Z)-2-Methoxy-3-{4-[2-(5-methyl-2-phenyl-oxazol-4-yl)-ethoxy]-benzo[b]thiophen-7-yl}-acrylic acid methyl ester 2.50 g of 3-hydroxy-2-methoxy-3-{4-[2-(5-methyl-2-phenyl-oxazol-4-yl)-ethoxy]-benzo[b]thiophen-7-yl}-propionic acid methyl ester (5.25 mmol, syn/anti mixture of 1:4) was dissolved at room temperature in 25 ml of DMF. After the addition of 0.59 ml of conc. sufuric acid (10.5 mmol), the brown solution was stirred at 100° C. for 15 h. During cooling the reaction solution to r.t., the product crystallized. Under stirring, 15 ml of methanol were added at r.t. and the suspension stirred for 1 h at 0° C. The white crystals were filtered off, washed with 25 ml of cold (−15° C.) methanol in two portions and dried to constant weight (20° C./5 mbar/16 h) to afford 2.13 g (90%) of the title compound with a purity of 99.5% (GC area).

Example 7

(Z)-2-Methoxy-3-{4-[2-(5-methyl-2-phenyl-oxazol-4-yl)-ethoxy]-benzo[b]thiophen-7-yl}-acrylic acid methyl ester In analogy to Example 6, 8.6×g of crude 3-hydroxy-2-methoxy-3-{4-[2-(5-methyl-2-phenyl-oxazol-4-yl)-ethoxy]-benzo[b]thiophen-7-yl}-propionic acid methyl ester (syn/anti=1:4) were isolated as a brown oil from 5.00 g of 4-[2-(5-methyl-2-phenyl-oxazol-4-yl)-ethoxy]-benzo[b]thiophen-7-carbaldehyde (13.66 mmol) and 3.17 ml of methoxyacetic acid methyl ester (31.4 mmol). This crude intermediate was dissolved at room temperature in 50 ml of DMF. Then 1.20 ml of conc. sulfuric acid (10.5 mmol) were added and the resulting dark brown solution was stirred at 100° C. for 15 h. The reaction solution was cooled to r.t., whereas the product crystallized. 50 ml of ethanol were added and the suspension stirred for 1 h at 0° C. The white crystals were filtered off, washed with 75 ml of cold (−15° C.) ethanol in two portions and dried to constant weight (20° C./5 mbar/16 h) to afford 4.812 g (77%) of the title compound with a purity of 98.3% (GC area).

Example 8

(Z)-2-Methoxy-3-{4-[2-(5-methyl-2-phenyl-oxazol-4-yl)-ethoxy]-benzo[b]thiophen-7-yl}-acrylic acid methyl ester To a solution of 3.17 ml methoxyacetic acid methyl ester (31.4 mmol) in 30 ml of THF, 3.5 ml of titanium tetrachloride (31.4 mmol) was added dropwise within 15 min at 0° C. After stirring the yellow solution for additional 15 min at the same temperature, 6.0 ml of N-ethyldiisopropylamine (34.1 mmol) were added within 5 min and the yellow/orange solution stirred for additional 15 min. A solution of 5.00 g of 4-[2-(5-methyl-2-phenyl-oxazol-4-yl)-ethoxy]-benzo[b]thiophen-7-carbaldehyde (13.66 mmol) in 70 ml of dichloromethane was added dropwise within 20 min and the the reaction mixture was stirred for additional 60 min. The reaction solution was allowed to warm up to r.t. and stirred the same temperature for 90 min, cooled to 0° C. and treated with 50 ml of ice water. The organic layer was separated, washed with 25 ml water, dried over sodium sulfate and evaporated to dryness to yield 8.15 g of crude 3-Hydroxy-2-methoxy-3-{4-[2-(5-methyl-2-phenyl-oxazol-4-yl)-ethoxy]-benzo[b]thiophen-7-yl}-propionic acid methyl ester ((syn/anti=6:4) as an orange oil. After this intermediate was dissolved at r.t. in 50 ml of DMF, 1.20 ml of conc. sulfuric acid (10.5 mmol) were added and the resulting dark brown solution was stirred at 100° C. for 17 h. The reaction solution was cooled to r.t., whereas the product crystallized. 50 ml of ethanol were added and the suspension stirred for 1 h at 0° C. The white crystals were filtered off, washed with 75 ml of cold (−15° C.) methanol in two portions and dried to constant weight (20° C./5 mbar/16 h) to afford 3.82 g (61%) of the title compound with a purity of 98.6% (GC area).

Example 9

(Z)-2-Methoxy-3-{4-[2-(5-methyl-2-phenyl-oxazol-4-yl)-ethoxy]-benzo[b]thiophen-7-yl}-acrylic acid To a suspension of 45.81 g of (Z)-2-methoxy-3-{4-[2-(5-methyl-2-phenyl-oxazol-4-yl)-ethoxy]-benzo[b]thiophen-7-yl}-acrylic acid methyl ester (100.9 mmol) in 920 ml of methanol, a solution of 40.15 g of potassium hydroxide (615.3 mmol) in 92 ml of water was added within 5 minutes. The white suspension was stirred for 90 min at 100° C. The formed yellowish reaction solution was cooled to 60° C., 54 ml of conc. hydrochloric acid were added dropwise within 5 min (pH 3-4) and the resulting thick suspension was cooled to 0° C. The solid was filtered off and washed with 1000 ml water in four portions. The filter cake was suspended in 920 ml of ethanol at 80° C. for 1 h and after at 0° C. for 2 h. The white crystals were filtered off, washed with 300 ml of cold (−15° C.) ethanol in two portions and dried to constant weight (20° C./5 mbar/16 h) to afford 41.66 g (95%) of the title compound with a purity of >99.9% according to HPLC (method described in Example 10). m.p.: 189-190° C. MS: 434.2 (M−H)⁻. $^1$H-NMR (CDCl$_3$): 2.41 (s, 3H); 3.11 (t, J=6.6, 2H); 3.79 (s, 3H); 4.47 (t, J=6.8, 2H); 6.88 (d, J=8.8, 1H); 7.30-7.40 (m, 2H); 7.40-7.47 (m, 3H); 7.49 (d, J=5.6, 1H); 8.00-8.10 (m, 2H); 8.12 (d, J=8.4, 1H); COOH very br.

Example 10

(S)-2-Methoxy-3-{4-[2-(5-methyl-2-phenyl-oxazol-4-yl)-ethoxy]-benzo[b]thiophen-7-yl}-propionic acid Asymmetric hydrogenation: In a glove box (O$_2$ content ≦2 ppm) 6.51 mg (0.00804 mmol) of [Ru(OAc)$_2$((S)-TMBTP)] were dissolved in 2 ml of methanol in a 5 ml flask. The resulting solution was stirred for 15 min. TMBTP is 4,4'-Bis(diphenylphosphino)-2,2',5,5'-tetramethyl-3,3'-dithiophene, its synthesis as (R) or (S) enantiomer is described in WO 96/01831 appl to Italfarmaco Sud and in T. Benincori et al, *J. Org. Chem.* 2000, 65, 2043. The complex [Ru(OAc)$_2$((+)-TMBTP)] has been synthesized in analogy to a general procedure reported in N. Feiken et al, *Organometallics* 1997, 16, 537, $^{31}$P-NMR (CDCl$_3$): 61.4 ppm (s).

A 185 ml stainless steel autoclave was charged in the same glove box with 7.0 g of (Z)-2-methoxy-3-{4-[2-(5-methyl-2-phenyl-oxazol-4-yl)-ethoxy]-benzo[b]thiophen-7-yl}-acrylic acid (16.1 mmol), 20 ml of dichloromethane, 10 ml of methanol, 3.21 ml of a 1 M NaOH aqueous solution (3.21 mmol) and the catalyst solution and the solution was rendered homogeneous. Finally, 18 ml of methanol were added and the solution became a suspension. The autoclave was sealed and the hydrogenation was run under stirring at 40° C. under 30 bar of hydrogen. After 6 h the autoclave was opened and the yellow-brown solution was rotary evaporated to dryness (50° C./5 mbar) to afford 7.27 g of crude product as a solid with an enantiomeric purity of 93% and a purity of 97.1% according to HPLC.

HPLC method for conversion determination: Chromolith Performance Merck column, 4.6×1000 mm, buffer solution of 10 mmol KH$_2$PO$_4$/liter water at pH 3, solvent A: water, solvent B: acetonitrile, solvent C: 300 ml buffer solution in 600 ml of acetonitrile, gradient from A/B/C 60/30/10% to 10/80/10% within 6 min, 1 min at 60/30/10, 2.5 ml/min, 267 nm. Retention times: Z-acid starting material 3.30 min, S-acid 3.76 min.

HPLC method for ee determination: Chiralpak-AD column, 25 cm×300 µm, 92% heptane/8% ethanol with 1.5% trifluoroacetic acid, flow 25 min at 5 µl/min, then 8 µl/min, 25° C., 267 nm. Retention times: R-acid 16.3 min, S-acid 18.4 min.

Example 11

Crude product of Example 10 has been worked-up and upgraded by isolation as an acid as follows:

Work-Up Procedure a):

A solution of 7.27 g (16.1 mmol) of crude product in 56 ml of tetrahydrofuran was treated at ca. 2° C. with 40.2 ml of a 1N NaOH aqueous solution (40.2 mmol). The resulting orange suspension was stirred at 22° C. for 1 h and then transferred to a separatory funnel which contained 90 ml of deionized water. The biphasic mixture was extracted with t-butyl methyl ether (116 ml in total), the aqueous phase was acidified with 8.41 ml of 25% hydrochloric acid and the resulting suspension extracted with 250 ml of dichloromethane. This solution was treated with decolorizing charcoal, filtered, concentrated at 40° C., then the temperature was reduced slowly to −10° C. whereas seed crystals were added. The resulting suspension was stirred over night at −10° C. and then filtered. The filter cake was washed with 15 ml of cold dichloromethane and dried to constant weight under high vacuum to afford 4.98 g (70.8%) of (S)-2-methoxy-3-{4-[2-(5-methyl-2-phenyl-oxazol-4-yl)-ethoxy]-benzo[b]thiophen-7-yl}-propionic acid of 98.2% ee. The mother liquor was evaporated to dryness and again crystallized from dichloromethane as above to afford 1.356 g of (S)-2-methoxy-3-{4-[2-(5-methyl-2-phenyl-oxazol-4-yl)-ethoxy]-benzo[b]thiophen-7-yl}-propionic acid of 76.2% ee. The two crystalline fractions were combined and dissolved in ethyl acetate at reflux. Slow cooling to room temperature within 6 hours with addition of seed crystals led to an abundant precipitation, which was completed in the refrigerator over night. Finally the precipitate was filtered and dried to constant weight as above to afford 5.684 g (80.8%) of (S)-2-Methoxy-3-{4-[2-(5-methyl-2-phenyl-oxazol-4-yl)-ethoxy]-benzo[b]thiophen-7-yl}-propionic acid of 99.0% ee. MS: 436.3 (M−H)⁻. NMR: (CDCl$_3$, 1H, δ, TMS) 2.40 (s, 3H), 3.06 (t, J=6.5, 2H), 3.20 (dd, J=7.5, J=14.5, 1H), 3.32 (s, 3H), 3.36 (dd, 1H), 4.20 (m, 1H), 4.36 (t, J=6.5, 2H), 6.74 (d, J=8, 1H), 7.15 (d, J=8, 1H), 7.32 (d, J=5.5, 1H), 7.40-7.45 (m, 3H), 7.48 (d, J=5.5, 1H), 7.97 (br d, J=8, 2H), COOH very br.

Work-Up Procedure B):

A solution of 7.74 g (16.1 mmol) of crude product in 56 ml of tetrahydrofuran was treated at ca. 2° C. with 40.2 ml of a 1N NaOH aqueous solution (40.2 mmol). The resulting orange suspension was stirred at 22° C. for 1 h and then transferred to a separatory funnel which contained 90 ml of deionized water. The biphasic mixture was extracted with t-butyl methyl ether (116 ml in total), the aqueous phase was acidified with 8.41 ml of 25% hydrochloric acid and the resulting suspension extracted with 252 ml of ethyl acetate. This solution was washed with water, dried (MgSO$_4$), treated with decolorizing charcoal, filtered, concentrated at 52° C. Then the temperature was reduced slowly within 2 h to room temperature under stirring whereas seed crystals were added. The suspension was cooled to −10° C. within 8 h, filtered and dried to constant weight as above to afford 5.643 g (80.2%) of (S)-2-methoxy-3-{4-[2-(5-methyl-2-phenyl-oxazol-4-yl)-ethoxy]-benzo[b]thiophen-7-yl}-propionic acid of 97.9% ee (fraction K1). The mother liquor was evaporated and the residue again crystallized from ethyl acetate as above to afford 0.702 g (10%) of (S)-2-methoxy-3-{4-[2-(5-methyl-2-phenyl-oxazol-4-yl)-ethoxy]-benzo[b]thiophen-7-yl}-propionic acid of 91.6% ee (fraction K2). Fraction K1 was recrystallized from ethyl acetate as described in procedure a) to afford a first crop consisting of 5.095 g (72.5%) of (S)-2-Methoxy-3-{4-[2-(5-methyl-2-phenyl-oxazol-4-yl)-ethoxy]-benzo[b]thiophen-7-yl}-propionic acid of 99.6% ee. Fraction K2 was also recrystallized as described in procedure a) to afford 0.513 g (7.3%) of (S)-2-Methoxy-3-{4-[2-(5-methyl-2-phenyl-oxazol-4-yl)-ethoxy]-benzo[b]thiophen-7-yl}-propionic acid of 98.4% ee.

Example 12

Crude material from Example 10 has been worked-up and upgraded with isolation as a diastereomeric salt as follows:

Procedure a):

To a solution of 11.75 g (26.8 mmol) of crude product in 60 ml of tetrahydrofuran was added dropwise at reflux (63-65%° C.) under stirring a solution of 3.452 g (28.2 mmol) of (S)-phenyl ethylamine (commercially available from Fluka) in 7 ml of tetrahydrofuran. Addition of seed crystals caused the immediate start of an abundant crystallization. The bath heating was switched off and the crystallization was completed over night at room temperature. The white crystals were filtered off, washed with 30 ml of cold (−20° C.) tetrahydrofuran and dried to constant weight (50° C./10 mbar, then 60°/0.5 mbar/8.5 h) to afford 13.4 g (88.9%) of (S)-2-methoxy-3-{4-[2-(5-methyl-2-phenyl-oxazol-4-yl)-ethoxy]-benzo[b]thiophen-7-yl}-propionic acid as (S)-phenyl ethylamine salt of 99.4% ee with 99.6% purity (HPLC area), mp. 157-158° C.

A suspension of 2.38 g of this (S,S)-salt in 25 ml of ethyl acetate was treated with 2.1 ml of 2 M hydrochloric acid and 5 ml of water. The resulting solution was stirred for 45 min at room temperature. Separation of the organic phase, washing of the aqueous phase with ethyl acetate, drying of the combined organic phases with sodium sulfate and evaporation of the solvent (10 mbar/45° C.) afforded 1.86 g (99.5%) of (S)-2-methoxy-3-{4-[2-(5-methyl-2-phenyl-oxazol-4-yl)-ethoxy]-benzo[b]thiophen-7-yl}-propionic acid of 99.5% ee with 99.7% purity (HPLC area).

Procedure b):

To a solution of 1.0 g (2.29 mmol) of crude product (92% ee, ca. 96% purity according to HPLC) in 6 ml of tetrahydrofuran was added dropwise under stirring at 50° C. a solution of 346 mg of L-norephedrin (2.29 mmol) in 3 ml of tetrahydrofuran. Within 1 h abundant crystals formed and the crystallization was completed at room temperature over night. After filtration, 0.91 g (67.6%) of (S)-2-methoxy-3-{4-[2-(5-methyl-2-phenyl-oxazol-4-yl)-ethoxy]-benzo[b]thiophen-7-yl}-propionic acid were isolated as the L-norephedrin salt of 99.6% ee with 99.0% purity (HPLC area), mp. 143-144° C.

Procedure c):

In analogy to procedure b), a solution of 1.0 g (2.29 mmol) of crude product (92% ee, ca. 96% purity according to HPLC) in 6 ml of tetrahydrofuran was treated with an equimolar amount of quinine to afford 0.90 g (51.7%) of (S)-2-methoxy-3-{4-[2-(5-methyl-2-phenyl-oxazol-4-yl)-ethoxy]-benzo[b]thiophen-7-yl}-propionic acid as quinine salt of 98.6% ee with 98.5% purity (HPLC area), mp. 129-131° C.

Procedure d):

In analogy to procedure b), a solution of 1.0 g (2.29 mmol) of crude product (92% ee, ca. 96% purity according to HPLC) in 10 ml of ethyl acetate was treated with an equimolar amount of cinconidine to afford after crystallization in the refrigerator 1.17 g (70%) of (S)-2-methoxy-3-{4-[2-(5-methyl-2-phenyl-oxazol-4-yl)-ethoxy]-benzo[b]thiophen-7-yl}-propionic acid as cinconidine salt of 93% ee with 96.4% purity (HPLC area), mp. 121-123° C.

Example 13

In an analogous manner to Example 10 but in the presence of (S)-phenylethylamine (2.29 mmol) instead of NaOH as a base, 5 g (11.48 mmol) of (Z)-2-methoxy-3-{4-[2-(5-methyl-2-phenyl-oxazol-4-yl)-ethoxy]-benzo[b]thiophen-7-yl}-acrylic acid were asymmetrically hydrogenated in 37 ml methanol/dichloromethane (3:2) in the presence of 0.93 mg of [Ru(OAc)$_2$((S)-TMBTP)] (S/C molar ratio 10'000) under 30 bar of hydrogen for 4 h at 40°, then 2 h at 60° h to reach 99.9% conversion. Rotary evaporation of the reaction mixture afforded quantitatively (S)-2-methoxy-3-{4-[2-(5-methyl-2-phenyl-oxazol-4-yl)-ethoxy]-benzo[b]thiophen-7-yl}-propionic acid of 91.8% ee with 99.4% purity (HPLC area). In analogy to example 13, the experiments described in table 1 have been carried out with different substrate-to-catalyst ratios.

TABLE 1

| Experiment No. | S/C | Purity of acid (HPLC %) | % e.e. (HPLC) |
|---|---|---|---|
| 13.1 | 3'000 | 98.0 | 91.7 (S) |
| 13.2 | 5'000 | 99.7 | 92.2 (S) |
| 13.3 | 15'000 | 97.6[1] | 91.2 (S) |
| 13.4 | 20'000 | 95.8[2] | 91.2 (S) |

[1] 99% conversion.
[2] 97% conversion.

Example 14

In an analogous manner to Example 10, 2.5 g (5.74 mmol) of (Z)-2-methoxy-3-{4-[2-(5-methyl-2-phenyl-oxazol-4-yl)-ethoxy]-benzo[b]thiophen-7-yl}-acrylic acid were asymmetrically hydrogenated in the presence of 3.22 mg of [Ru(OAc)₂((S)-6-MeO-2-naphthyl)-MeOBIPHEP)] (S/C molar ratio 2000) at 40° C. under 15 bar of hydrogen for 24 h to reach 99.6% conversion. Rotary evaporation of the reaction mixture afforded quantitatively (S)-2-methoxy-3-{4-[2-(5-methyl-2-phenyl-oxazol-4-yl)-ethoxy]-benzo[b]thiophen-7-yl}-propionic acid of 75.8% ee with 98.5% purity (HPLC area).

To a solution of 6.50 g (15.8 mmol) of crude product in 33 ml of tetrahydrofuran was added dropwise at reflux (63-65%° C.) under stirring a solution of 1.91 g (15.6 mmol) of (S)-phenyl ethylamine (commercially available from Fluka) in 3 ml of tetrahydrofuran. Addition of seed crystals and turning off the bath heating brought about the start of the crystallization. The crystallization was completed over night at room temperature, the white crystals were filtered off, washed with 20 ml of cold (−20° C.) tetrahydrofuran and dried to constant weight (50° C./10 mbar/6 h) to afford 6.57 g (79.2%) of (S)-2-methoxy-3-{4-[2-(5-methyl-2-phenyl-oxazol-4-yl)-ethoxy]-benzo[b]thiophen-7-yl}-propionic acid as (S)-phenyl ethylamine salt of 96.3% ee with 99.9% purity (HPLC area), with a mp. of 157-159.5° C.

Example 15

In a glove box (O₂ content ≦2 ppm) a 35 ml autoclave equipped with a 3 ml glass insert and a magnetic stirring bar was charged with 50 mg (0.11 mmol) of (Z)-2-methoxy-3-{4-[2-(5-methyl-2-phenyl-oxazol-4-yl)-ethoxy]-benzo[b]thiophen-7-yl}-acrylic acid, 2.6 mg of [Ru(OAc)₂((S)-6-MeO-2-naphthyl)-MeOBIPHEP)] and 1 ml of ethanol. The asymmetric hydrogenation was run for 3 h at 60° C. under 60 bar of hydrogen to achieve 97.5% conversion. HPLC analysis showed that the resulting (S)-2-methoxy-3-{4-[2-(5-methyl-2-phenyl-oxazol-4-yl)-ethoxy]-benzo[b]thiophen-7-yl}-propionic acid had 97.5% purity and 71% ee.

Example 16

In a manner analogous to example 15 the following hydrogenations were performed with (Z)-2-methoxy-3-{4-[2-(5-methyl-2-phenyl-oxazol-4-yl)-ethoxy]-benzo[b]thiophen-7-yl}-acrylic acid as the substrate in the presence of ruthenium complexes of general formula [Ru(OAc)₂(Diphosphine)] as the catalyst. The reaction mixture was evaporated to dryness, the residue was dissolved in ethyl acetate, the resulting solution was filtered through silica gel and analyzed as described in Example 10 to determine the conversion and the ee of the resulting (S)-2-methoxy-3-{4-[2-(5-methyl-2-phenyl -oxazol-4-yl)-ethoxy]-benzo[b]thiophen-7-yl}-propionic acid. The obtained results are reported in Table 1.

TABLE 2

| Experiment No. | Chiral Diphosphine | Purity of acid (HPLC %) | % e.e. (HPLC) |
|---|---|---|---|
| 16.1 | (S)-TMBTP | 99 | 89 (S) |
| 16.2 | (R)-(2,2)-PHANEPHOS | >99 | 63 (S) |
| 16.3 | (R)-MeOBIPHEP | >99 | 56 (R) |
| 16.4 | (S)-(2-Naphtyl)-MeOBIPHEP[1] | 99 | 68 (S) |
| 16.5 | (R)-TriMeOBIPHEP | 95 | 69 (R) |
| 16.6 | (S)-BIPHEMP | 95 | 68 (S) |
| 16.7 | (R)-BnOBIPHEP | 95 | 64 (R) |
| 16.8 | (R)-BenzoylOBIPHEP | 99 | 64 (R) |
| 16.9 | (S)-pTol-BIPHEMP | 95 | 62 (S) |
| 16.10 | (S)-MeOBIPHEP | 95 | 61 (S) |
| 16.11 | (R)-tButylCOOBIPHEP | 99 | 59 (R) |
| 16.12 | (R)-iPrOBIPHEP | 97 | 58 (R) |
| 16.13 | (R)-pPhenyl-MeOBIPHEP | 98 | 55 (R) |
| 16.14 | (R,R,S,S)-Mandyphos[2] | 99 | 55 (S) |
| 16.15 | (R)-pAn-MeOBIPHEP | 97 | 54 (R) |
| 16.16 | (S)-3,5-Xyl-MeOBIPHEP | 99 | 53 (S) |
| 16.17 | (S)-pTol-MeOBIPHEP | 99 | 52 (S) |
| 16.18 | (S)-3,5-Xyl-BIPHEMP | 99 | 51 (S) |
| 16.19 | (S)-BINAP | 93 | 51 (S) |
| 16.20 | (S)-2-Thienyl-MeOBIPHEP | 98 | 42 (S) |

0.44 g (1 mmol) scale in a 35 ml autoclave, 40° C., 60 bar, 6 h, S/C 500, 99.2% conversion.

Catalyst prepared in situ from [Ru(COD)(OAc)₂] and the diphosphine in ethanol.

Example 17

In a manner analogous to example 15 the following hydrogenations were performed with (Z)-2-methoxy-3-{4-[2-(5-methyl-2-phenyl-oxazol-4-yl)-ethoxy]-benzo[b]thiophen-7-yl}-acrylic acid as the substrate in the presence of ruthenium complexes of general formula [Ru(OAc)₂(Diphosphine)] as the catalyst in various solvents. The reaction mixture was worked-up and analyzed as described in Example 16. If present, the second row of results for a single diphosphine was obtained by addition of 1 molar equivalent (0.11 mmol) of triethylamine. In all instances the conversion was ≧95%. The obtained ee values are reported in Table 2.

TABLE 3

| Chiral Diphosphine | EtOH | CH₂Cl₂ | THF | AcOEt | Toluene |
|---|---|---|---|---|---|
| (S)-BIPHEMP | 68 (S) | 61 (S) | 60 (S) | 60 (S) | 78 (S) |
|  | 67 (S) |  |  |  | 64 (S) |
| (S)-pTol-BIPHEMP | 62 (S) | 65 (S) | 66 (S) | 64 (S) | 73 (S) |
| (R)-TriMeOBIPHEP | 69 (R) | 63 (R) | 62 (R) | 66 (R) | 61 (R) |
| (R)-BnOBIPHEP | 64 (R) | 53 (R) | 52 (R) | 54 (R) | 56 (R) |
| (S)-(6-MeO-2-Naphtyl)-MeOBIPHEP | 73 (S) | 61 (S) | 62 (S) | 67 (S) | 71 (S) |
|  | 73 (S) |  |  |  | 70 (S) |
| (R)-TMBTP | 89 (R) | 85 (R) | 73 (R) | 76 (S) | 66 (R) |
|  | 88 (R) |  |  |  | 68 (R) |

Example 18

In a glove box (O₂ content ≦2 ppm) a 35 ml autoclave equipped with a magnetic stirring bar was charged with 300-436 mg of (Z)-2-methoxy-3-{4-[2-(5-methyl-2-phenyl-oxazol-4-yl)-ethoxy]-benzo[b]thiophen-7-yl}-acrylic acid in ethanol and the necessary amount of [Ru(OAc)₂((S)-TMBTP)] to achieve the reported S/C ratio. The asymmetric hydrogenation was run for 6 h at the temperature and pressure reported in Table 3. The reaction mixture was worked-up and analyzed as described in Example 16.

TABLE 4

| Exp. | S/C | Base (equiv) | C (% w/w) | T (° C.) | P (bar) | Conversion (%, HPLC) | e.e. (%(S)) |
|---|---|---|---|---|---|---|---|
| 18.1 | 500 | — | 5 | 60 | 60 | 100 | 90 |
| 18.2 | 1000 | $Et_3N$ (0.5) | 5 | 60 | 60 | 98.9 | 85 |
| 18.3 | 1000 | $NaOCH_3$ (0.5) | 5 | 60 | 60 | 100 | 89 |
| 18.4 | 1000 | $NaOCH_3$ (0.5) | 10 | 20 | 60 | 93 | 92 |
| 18.5 | 1000 | $NaOCH_3$ (0.5) | 10 | 20 | 30 | 90 | 93 |
| 18.6[1)] | 1000 | $NaOCH_3$ (0.5) | 9.5 | 20 | 60 | 93 | 92 |
| 18.7[2)] | 1000 | $NaOCH_3$ (0.5) | 7.3 | 20 | 60 | 99.7 | 93 |

Solvent is 3 ml MeOH and 2 ml $CH_2Cl_2$
Solvent is 2 ml MeOH and 3 ml $CH_2Cl_2$

Example 19

In a glove box ($O_2$ content ≦2 ppm) a 185 ml autoclave equipped with a mechanical stirrer was charged with (Z)-2-methoxy-3-{4-[2-(5-methyl-2-phenyl-oxazol-4-yl)-ethoxy]-benzo[b]thiophen-7-yl}-acrylic acid, solvent, base and the necessary amount of [Ru(OAc)$_2$((S)-TMBTP)] to achieve the reported S/C ratio. Sodium methylate (NaOMe) was added as a methanolic solution (Fluka prakt. Catalogue Nr. 71748) whereas NaOH, KOH and $Na_2HPO_4$ were added as 1 M aqueous solutions. The asymmetric hydrogenation was run at the temperature and pressure reported in Table 4. The reaction mixture was worked-up and analyzed as described in Example 16.

TABLE 5

| Exp. Nr. | Scale (g) | Base (equiv) | S/C | T ° C. | P bar | Solvent ml | c % w/w | t h | Conv. % HPLC | e.e. % S |
|---|---|---|---|---|---|---|---|---|---|---|
| 19.1 | 5.0 | NaOMe 0.44 | 1000 | 20 | 30 | EtOH 50 | 11.2 | 26.5 | 99.0 | 93.0 |
| 19.2 | 5.0 | NaOMe 0.44 | 1000 | 20 | 60 | EtOH 50 | 11.2 | 26 | 99.4 | 93.6 |
| 19.3 | 2.5 | NaOMe 0.44 | 2000 | 20 | 60 | MeOH 5 $CH_2Cl_2$ 20 | 7.6 | 23 | 97.8 | 91.3 |
| 19.4 | 2.5 | NaOMe 0.20 | 2000 | 40 | 60 | MeOH 10 $CH_2Cl_2$ 15 | 8.3 | 6 | 97.7 | 90.6 |
| 19.5 | 2.5 | NaOMe 0.05 | 2000 | 40 | 60 | MeOH 10 $CH_2Cl_2$ 15 | 8.3 | 6 | 98.0 | 90.3 |
| 19.6 | 2.5 | NaOMe 0.10 | 2000 | 20 | 60 | MeOH 10 $CH_2Cl_2$ 15 | 8.3 | 22 | 96.5 | 90.4 |
| 19.7 | 2.5 | NaOMe 0.10 | 2000 | 20 | 60 | MeOH 25 | 11.2 | 22.5 | 71.0 | 93.7 |
| 19.8 | 5 | NaOMe 0.10 | 2000 | 40 | 60 | MeOH 30 $CH_2Cl_2$ 20 | 9.0 | 23.5 | 98.0 | 92.3 |
| 19.9 | 2.5 | NaOMe 0.20 | 2000 | 40 | 60 | MeOH 15 $CH_2Cl_2$ 10 | 9.0 | 6 | 98.1 | 91.8 |
| 19.10 | 2.5 | NaOH 0.10 | 2000 | 40 | 60 | MeOH 15 $CH_2Cl_2$ 10 | 9.0 | 6 | 97.3 | 91.8 |
| 19.11 | 2.5 | NaOH 0.20 | 2000 | 40 | 60 | MeOH 15 $CH_2Cl_2$ 10 | 9.0 | 6 | 98.5 | 92.2 |
| 19.12 | 2.5 | NaOH 0.20 | 2000 | 20 | 30 | MeOH 15 $CH_2Cl_2$ 10 | 9.0 | 6.5 | 61.4 | 94.1 |
| 19.13 | 7.0 | NaOH 0.20 | 2000 | 40 | 60 | MeOH 30 $CH_2Cl_2$ 20 | 12.2 | 6 | 98.7 | 92.7 |
| 19.14 | 5.0 | NaOH 0.20 | 2000 | 40 | 60 | MeOH 12 $CH_2Cl_2$ 8 | 19.9 | 6 | 95.2 | 92.9 |
| 19.15 | 2.5 | $Et_3N$ 0.10 | 2000 | 40 | 60 | MeOH 15 $CH_2Cl_2$ 10 | 9.0 | 23.5 | 96.5 | 91.3 |
| 19.16 | 2.5 | $Et_3N$ 0.20 | 2000 | 40 | 60 | MeOH 15 $CH_2Cl_2$ 10 | 9.0 | 6 | 97.9 | 92.0 |
| 19.17 | 2.5 | $Na_2HPO_4$ 0.20 | 2000 | 40 | 60 | MeOH 15 $CH_2Cl_2$ 10 | 9.0 | 5 | 97.8 | 91.5 |
| 19.18 | 2.5 | KOH 0.20 | 2000 | 40 | 60 | MeOH 15 $CH_2Cl_2$ 10 | 9.0 | 5 | 98.1 | 92.0 |
| 19.19 | 2.5 | NaOH 0.2 | 2000 | 40 | 15 | MeOH 15 $CH_2Cl_2$ 10 | 9.0 | 6 | 98.0 | 92.9 |
| 19.20 | 2.5 | NaOH 0.2 | 2000 | 40 | 5 | MeOH 15 $CH_2Cl_2$ 10 | 9.0 | 24 | 70.0 | 91.5 |

1.2 ml of water added;

Example 20

In a glove box ($O_2$ content ≦2 ppm) a 185 ml autoclave equipped with a mechanical stirrer was charged with 1 g of (Z)-2-methoxy-3-{4-[2-(5-methyl-2-phenyl-oxazol-4-yl)-ethoxy]-benzo[b]thiophen-7-yl}-acrylic acid, MeOH 15 ml/$CH_2Cl_2$ 10 ml as solvent (c=3.8% w/w), base and the necessary amount of [Ru(OAc)$_2$((S)-TMBTP)] to achieve the reported S/C ratio. NaOH was added as 1 M aqueous solution. The asymmetric hydrogenation was run at the temperature and pressure reported in Table 5.

TABLE 6

| Exp. No. | Catalyst | base (equiv) | S/C | T °C. | p bar | t h | Conv. % HPLC | e.e. % S |
|---|---|---|---|---|---|---|---|---|
| 20.1 | Ru(OAc)$_2$((S)-TMBTP) | NaOH 0.20 | 2000 | 40 | 60 | 6 | 98.5 | 90.1 |
| 20.2 | Ru(TFA)$_2$((S)-TMBTP) | NaOH 0.20 | 1000 | 40 | 60 | 9 | 98.4 | 91.1 |
| 20.3 | Ru(TFA)$_2$((S)-BIPHEMP) | NaOH 0.20 | 2000 | 40 | 60 | 4 | 98.5 | 67.7 |
| 20.4 | Ru(OAc)$_2$((S)-BIPHEMP) | NaOH 0.20 | 2000 | 40 | 60 | 4 | 98.6 | 67.9 |
| 20.5 | Ru(TFA)$_2$((S)-MeOBIPHEP) | NaOH 0.20 | 2000 | 40 | 60 | 4 | 98.7 | 63.6 |
| 20.6 | Ru(OAc)$_2$((S)-MeOBIPHEP) | NaOH 0.20 | 2000 | 40 | 60 | 4 | 98.6 | 62.9 |
| 20.7 | Ru(TFA)$_2$((S)-TriMeOBIPHEP) | NaOH 0.20 | 2000 | 40 | 60 | 4 | 98.5 | 71.4 |
| 20.8 | Ru(OAc)$_2$((S)-(6-MeO-2-Naphtyl)-MeOBIPHEP) | NaOH 0.20 | 2000 | 40 | 60 | 4 | 99.8 | 71.5 |

Example 21

In a glove box ($O_2$ content ≦2 ppm) in a measuring flask 9.3 mg (0.023 mmol) of [Rh(cyclooctadiene)$_2$]BF$_4$ were dissolved in 8 ml of tetrahydrofuran and 2 ml of methanol. In the glass insert of a 2.5 ml autoclave equipped with a magnetic stirring 1 ml of the [Rh(cyclooctadiene)$_2$] BF$_4$ solution was added to the amount of chiral diphosphine corresponding to 0.0023 mmol and the in situ formed catalyst solution stirred at 40° C. for ca. 1 h. Then 50 mg (0.11 mmol) of (Z)-2-methoxy-3-{4-[2-(5-methyl-2-phenyl-oxazol-4-yl)-ethoxy]-benzo[b]thiophen-7-yl}-acrylic acid were added and the autoclave was sealed and pressurized with hydrogen. The asymmetric hydrogenation was run for 3 h at 60° C. under 60 bar of hydrogen. The reaction mixture was worked-up and analyzed as described in Example 15. The results are reported in Table 6.

TABLE 7

| Exp. No. | Chiral Diphosphine | Purity of acid (HPLC %) | % e.e. (HPLC) |
|---|---|---|---|
| 21.1 | (R,S)-PPCr-P(tBu)2 | 99.3 | 62 (S) |
| 21.2 | (R,S)-BPPFA-EPIP | 92.5 | 80 (S) |
| 21.3 | (S,R)-BPPFA-EDMA | 90.0 | 78 (R) |
| 21.4 | (R,S)-(2-Furyl)-PPFA-P(Cyp)$_2$ | 99.4 | 77 (R) |
| 21.5 | (R,S)-(2-Furyl)-PPFA-P(Cy)2 | 99.2 | 74 (R) |
| 21.6 | (S,S,S,S)-Me-f-KetalPhos | 99.5 | 55 (S) |
| 21.7 | (R)-TMBTP | 55.2 | 58 (S) |
| 21.8 | (R)-3,5-tBu,4-MeO-MeOBIPHEP | 99.1 | 57 (S) |

Example 22

In a manner analogous to Example 21 the following hydrogenations were performed with (Z)-2-methoxy-3-{4-[2-(5-methyl-2-phenyl-oxazol-4-yl)-ethoxy]-benzo[b]thiophen-7-yl}-acrylic acid as the substrate in the presence of the in situ formed catalyst solution prepared from [Rh(cyclooctadiene)$_2$]BF$_4$ and the chiral diphosphine in various solvents. The reaction mixture was worked-up and analyzed as described in Example 16. The results are summarized in Table 7, where for each experiment the ee values are reported and the conversions are written in parentheses.

TABLE 8

| Chiral Diphosphine | THF | AcOEt | $CH_2Cl_2$ | MeOH | Toluene | Dioxane |
|---|---|---|---|---|---|---|
| (R)-(2-Furyl)-MeOBIPHEP | 74 (31)[1] | 67 (13) | 84 (19) | 64 (19) | 61 (13)[2] | 70 (29) |
| (R,S)-BPPFA-EPIP | 80 (100)[1] | 76 (100) | 67 (100) | 74 (83) | 70 (94) | 67 (100) |
| (R,S)-(2-Furyl)-PPFA-P(Cyp)$_2$[3] | 77 (100)[1] | 16 S (36) | — (6) | 51 (91) | 14 (75) | 68 (95) |
| (R)-3,5-tBu,4-MeO-MeOBIPHEP | 57 (100)[1] | 56 (88) | 42 (15) | 33 (92) | 57 (35) | 60 (80) |
| (R,S)-PPCr-P(tBu)$_2$ | 62 (100)[1] | 56 (100) | 57 (100) | 65 (73) | 65 (100)[2] | 56 (100) |
| (S,S,S)-Me-f-KetalPhos | 55 (100)[1] | 22 (12) | 33 (16) | 47 (91) | 49 (100)[2] | 36 (56) |

TABLE 8-continued

| Chiral Diphosphine | THF | AcOEt | CH$_2$Cl$_2$ | MeOH | Toluene | Dioxane |
|---|---|---|---|---|---|---|
| (R,S)-BPPFA-EPIP | 67 (100)[4)] | — | — | — | — | |
| (R,S)-(2-Furyl)-PPFA-P(Cyp)$_2$[3)] | 74 (100)[4)] | — | — | — | — | — |

THF/MeOH 4/1
Toluol/MeOH 10/1
Product has (R) configuration
Solvent is THF containing 0.1 mmol of triethylamine, rhodium salt is [RhCl(1,5-cyclooctadiene)]$_2$, Example 23

Tributylammonium Hydroxy-(4-hydroxy-benzo[b]thiophen-7-yl)-acetate

A 2 L reactor equipped with a mechanical stirrer, a thermometer, a dropping funnel, a sensor connected to a pH-meter and an argon inlet was charged under argon with 76.2 g (500 mmol) of 4-Hydroxybenzothiophene and 617.1 g (1100 mmol) of a 10% KOH aqueous solution. To the dark solution were added at 0-5° C. within 30 min ca. 85.91 g (580 mmol) of a 50% glyoxylic acid solution in water. If necessary, more glyoxylic acid is added such that the pH of the solution at the end of the addition was 11.5. After stirring for 3 h at 0-5° C., 200 ml of tert-butyl methyl ether were added to the reaction mixture followed by ca. 70 ml of 25% HCl solution in water such that the pH was ca. 7.0. The biphasic mixture was filtered through Speedex, then ca. 70 ml of 25% HCl solution in water were added to the aqueous phase such that the pH was ca. 2.0. After addition of 450 ml of tert-butyl methyl ether the organic phase was separated at room temperature and the aqueous phase washed with tert-butyl methyl ether. The combined organic phases were concentrated to a volume of ca. 300 ml and the residue was diluted with 50 ml of tert-butyl methyl ether and 100 ml of acetonitrile. To the resulting clear solution was added portionswise at 20-30° C. within 1 h a solution of 93.6 g (500 mmol) of tributylamine in 100 ml of tert-butyl methyl ether under seeding with crystals of the product. The resulting suspension was stirred over night at 20-30° C. and then filtered off. The filter cake was washed with 160 ml of tert-butyl methyl ether/acetonitrile 3:1 and the crystals dried over night at 60° C./10 mbar to afford 108.9 g (53.1%) of tributylammonium hydroxy-(4-hydroxy-benzo[b]thiophen-7-yl)-acetate as white crystals with a m.p. of ca. 200° C. (dec.).

4-hydroxy-benzo[b]thiophene-7-carboxaldehyde

A 750 ml, 4-necked glass flask equipped with a mechanical stirrer, a thermometer, a dropping funnel and an argon inlet was charged under argon with 41.0 g (100 mmol) of tributylammonium hydroxy-(4-hydroxy-benzo[b]thiophen-7-yl)-acetate, 60.5 g (115 mmol) of iron(III) sulfate and a mixture prepared from 60 ml of dry ethanol and 300 ml of 0.4 N sulfuric acid aqueous solution. Then stirring was started and the reaction mixture was heated to 55-60° C. for 5 h. After cooling to room temperature, 300 ml of isopropyl acetate and 100 ml of water were added under stirring, then the organic phase was separated and transferred into a 500 ml glass flask equipped with a pH meter. After addition of 150 ml of water (pH was 3.0), ca. 58 ml of a 2 N sodium hydroxide aqueous solution were added dropwise at 20° C. until a pH of 12-12.5 was reached. The organic phase was removed and to the aqueous phase was added at 10-15° C. dropwise ca. 54 ml of a 2 N aqueous solution of sulfuric acid until a pH of 4-4.5 was reached. The product precipitated during the addition. The suspension was stirred over night at room temperature, 1.2 h in an ice bath and then filtered. The filter cake was washed with water and dried at 60° C./15 mbar to afford 17.23 g (94%) of 4-hydroxy-benzo[b]thiophene-7-carboxaldehyde as white crystals with m.p. of 204° C.

4-[2-(5-methyl-2-phenyl-4-oxazolyl)ethoxy]-benzo[b]thiophene-7-carboxaldehyde

A 750 ml glass flask equipped with a thermometer, a stirrer and an argon inlet was charged under argon with 9.32 g (50 mmol) of 4-hydroxy-benzo[b]thiophene-7-carboxaldehyde, 7.60 g (55 mmol) of potassium carbonate and 135 ml of DMF. The resulting suspension was heated with stirring to 86° C., then a solution of 12.24 g (50 mmol) of 2-(5-methyl-2-phenyl)-4-oxazolyl)ethanol methanesulfonyl ester in 75 ml of DMF was added at this temperature within 60 min. The reaction mixture was stirred at the same temperature for 6 h, then 90 ml of toluene followed by 300 ml of water were added dropwise within 15 min, whereas the temperature was kept above 75° C. The aqueous phase was separated and extracted with 30 ml of warm toluene. The two toluene phases were combined, re-extracted with water, transferred into a 500 ml glass flask and finally treated with 180 ml of methanol. The resulting suspension was stirred over night at room temperature and 2 h at −13° C. Then the suspension was filtered, the filter cake was washed with toluene, cool methanol and finally dried at 60° C./10 mbar to afford 15.19 g (83%) of 4-[2-(5-methyl-2-phenyl-4-oxazolyl)ethoxy]-benzo[b]thiophene-7-carboxaldehyde as colorless crystals with a m.p. of 154° C.

4-[2-(5-methyl-2-phenyl-4-oxazolyl)ethoxy]-benzo[b]thiophene-7-carbaldehyde

A 2 l, 4-necked glass reactor equipped with a mechanical stirrer, a thermometer, a cooler, a dropping funnel and an argon inlet was charged under argon in sequence with 103.2 g (250 mmol) of tributylammonium hydroxy-(4-hydroxy-benzo[b]thiophen-7-yl)-acetate, 151.3 g (287 mmol) of iron (III) sulfate, 150 ml of isopropanol, a mixture of 750 ml of water and 150 ml of 2 N sulfuric acid. The reaction mixture was heated under stirring to 63-65° C. for 2 h. After cooling to room temperature, 600 ml of isopropyl acetate were added and the mixture filtered. The filtrate was washed with 100 ml of water, then the organic phase was concentrated (ca. 470 ml were distilled off at 50° C./150-50 mbar). After addition of 625 ml of DMF, the rest of more volatile solvents are removed completely at 50° C./150-50 mbar. The water content at this point was less than 0.4%. This suspension containing the intermediate 4-hydroxy-benzo[b]thiophene-7-carboxaldehyde was transferred with aid of 660 ml of DMF in a 4 l reactor (equipped as the 2l reactor above) which had been charged with 38.0 g of potassium carbonate. To the dark suspension was added within 60 min at 86-90° C. a solution of 70.4 g (250 mmol) of 2-(5-methyl-2-phenyl)-4-oxazolyl)ethanol methanesulfonyl ester in 275 ml of DMF. The reaction mixture was stirred at the same temperature for 6 h, then 450 ml of toluene followed by 950 ml of water were added, whereas the temperature was kept above 75° C. The aqueous phase was separated and extracted with 150 ml of warm toluene. The two toluene phases were combined, re-extracted with water and finally treated at a temperature between 65 and 40° C. with 900 ml of methanol. The resulting suspension was stirred for 1 h at 40° C., cooled to −15° C. and stirred for 3 h at −15° C. Finally the suspension was filtered, the filter cake was washed with 100 ml of a cold (−15° C.) toluene/methanol mixture and dried at 60° C./10 mbar to afford 76.8 g (84.5%) of 4-[2-(5-methyl-2-phenyl-4-oxazolyl)ethoxy]-benzo[b]thiophene-7-carbaldehyde as colorless crystals with a m.p. of 154° C.

What is claimed is:

1. A process for the preparation of a compound of formula (I)

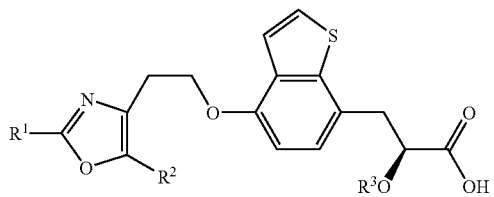

(I)

or salts thereof, comprising catalytic asymmetric hydrogenation of a compound of formula (II)

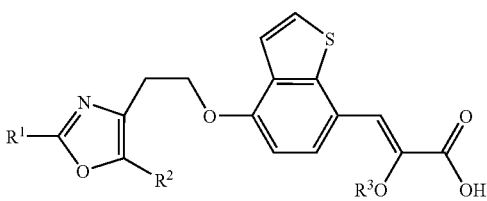

(II)

or salts thereof, in the presence of a catalyst comprising ruthenium and a chiral diphosphine ligand or comprising rhodium and a chiral diphosphine ligand, to yield said compound of formula (I), wherein
$R^1$ is aryl or heteroaryl,
$R^2$ is lower-alkyl,
$R^3$ is lower-alkyl.

2. The process of claim 1, wherein the the chiral diphosphine ligand is selected from formula (III), (IV), (V), (VI) or (VII)

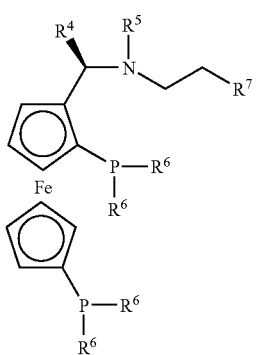

(III)

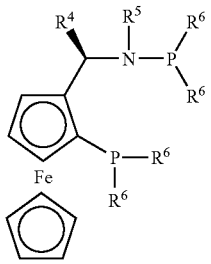

(IV)

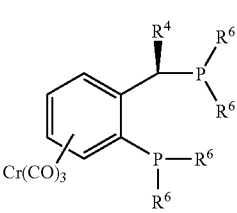

(V)

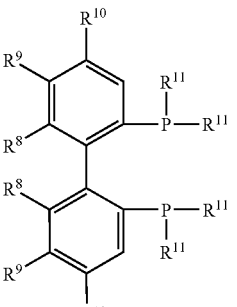

(VI)

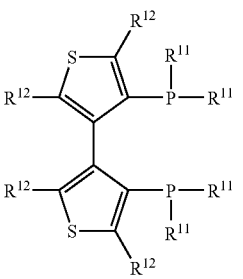

(VII)

wherein
$R^4$ is lower-alkyl;
$R^5$ is lower-alkyl;
$R^6$ independently is aryl, heteroaryl, cylcoalkyl or lower-alkyl;
$R^7$ is N(lower-alkyl)$_2$ or piperidinyl;
$R^8$ is lower-alkyl, lower-alkoxy, hydroxy or lower-alkyl-C(O)O—;
$R^9$ and $R^{10}$ independently are hydrogen, lower-alkyl, lower-alkoxy or di(lower-alkyl)amino; or
$R^8$ and $R^9$ or $R^9$ and $R^{10}$ which are attached to the same phenyl group, or both $R^8$ attached to different phenyl groups, taken together, are —X—(CH$_2$)$_n$—Y—, wherein X is —O— or —C(O)O—, Y is —O— or —N(lower-alkyl)- and n is an integer from 1 to 6; or
$R^8$ and $R^9$, or $R^9$ and $R^{10}$, together with the carbon atoms to which they are attached, form a naphthyl, tetrahydronaphthyl or dibenzofuran ring;
$R^{11}$ independently is phenyl or napthyl, substituted with 0 to 7 substituents independently selected from the group consisting of lower-alkyl, lower-alkoxy, di(lower-alkyl)amino, morpholino, phenyl and tri(lower-alkyl)silyl; $R^{12}$ independently is lower-alkyl with the proviso that when $R^{11}$ is phenyl then it is substituted by 0 to 5 substituents.

3. The process of claim 2, wherein the catalyst is of the formula [Ru(chiral diphosphine)B$_2$], wherein the chiral diphosphine is characterised by formula (VI) or (VII) as defined in claim 2 and wherein B is CH$_3$COO$^-$, CF$_3$COO$^-$ or a halogenide.

4. The process of claim 3, wherein the chiral diphosphine is selected from the group consisting of (S)-MeOBIPHEP, (S)-BIPHEMP, (S)-TMBTP, (S)-(2-Naphthyl)-MeOBIPHEP, (S)-(6-MeO-2-Naphthyl)-MeOBIPHEP, (S)-TriMeOBIPHEP, (R,R,S,S)-Mandyphos, (S)-BnOBIPHEP, (S)-BenzoylBIPHEP, (S)-pTol-BIPHEMP, (S)-tButylCOOBIPHEP, (S)-iPrOBIPHEP, (S)-pPhenyl-MeOBIPHEP, (S)-pAn-MeOBIPHEP, pTol-MeOBIPHEP, (S)-3,5-Xyl-MeOBIPHEP, (S)-3,5-Xyl-BIPHEMP, (S)-BINAP and (S)-2-Furyl-MeOBIPHEP.

5. The process of claim 4, wherein the chiral diphosphine is (S)-TMBTP, (S)-(2-Naphthyl)-MeOBIPHEP or (S)-(6-MeO-2-Naphthyl)-MeOBIPHEP.

6. The process of claim 3, wherein B is CH$_3$COO$^-$ or CF$_3$COO$^-$.

7. The process of claim 6, wherein the catalyst is selected from the group consisting of [Ru(CH$_3$COO$^-$)$_2$((S)-TMBTP)], [Ru(CF$_3$COO$^-$)$_2$((S)-TMBTP)], [Ru(CH$_3$COO$^-$)$_2$((S)-(2-Naphthyl)-MeOBIPHEP)], [Ru(CF$_3$COO$^-$)$_2$((S)-(2-Naphthyl)-MeOBIPHEP)], [Ru(CH$_3$COO$^-$)$_2$((S)-(6-MeO-2-Naphthyl)-MeOBIPHEP)] and [Ru(CF$_3$COO$^-$)$_2$((S)-(6-MeO-2-Naphthyl)-MeOBIPHEP)].

8. The process of claim 7, wherein the catalytic hydrogenation is carried out at a pressure of 20 to 40 bar.

9. The process of claim 8, wherein the catalytic hydrogenation is carried out at a temperature of 20 to 60° C.

10. The process of claim 9, wherein the catalytic hydrogenation is carried out in the presence of a base.

11. The process of claim 10, wherein the catalytic hydrogenation is carried out in a solvent which is selected from methanol, dichloromethan, ethanol, tetrahydrofuran, ethylacetat or toluene, or a combination thereof.

12. The process of claim 11, wherein the catalytic hydrogenation is carried out in a solvent which is a 3:2 mixture of methanol and dichloromethan.

13. The process of claim 12, comprising crystallisation of the compound of formula (I).

14. The process of claim 13, comprising crystallisation of the compound of formula (I) as a salt with a primary amine.

15. The process of claim 14, wherein the primary amine is (S)-phenylethylamine.

16. The process of claim 15, wherein the compound of formula (I) is(S)-2-methoxy-3-{4-[2-(5-methyl-2-phenyl-oxazol-4-yl)-ethoxy]-benzo[b]thiophen-7-yl}-propionic acid.

17. The process of claim 16, comprising the conversion of the compound of formula (I) into a pharmaceutically acceptable salt.

18. The process of claim 15, wherein $R^1$ is phenyl.

19. The process of claim 18, wherein $R^2$ is methyl.

20. The process of claim 19, wherein $R^3$ is methyl.

21. A process for the preparation of (S)-2-methoxy-3-{4-[2-(5-methyl-2-phenyl-oxazol-4-yl)-ethoxy]-benzo[b]thiophen-7-yl}-propionic acid, comprising a) reacting 4-[2-(5-methyl-2-phenyl-oxazol-4-yl)-ethoxy]-benzo[b]thiophen-7-carbaldehyde with methoxyacetic acid methyl ester to yield 3-hydroxy-2-methoxy-3-{4-[2-(5-methyl-2-phenyl-oxazol-4-yl)-ethoxy]-benzo[b]thiophen-7-yl}-propionic acid methyl ester;

b) converting 3-hydroxy-2-methoxy-3-{4-[2-(5-methyl-2-phenyl-oxazol-4-yl)-ethoxy]-benzo[b]thiophen-7-yl}-propionic acid to (Z)-2-methoxy-3-{4-[2-(5-methyl-2-phenyl-oxazol-4-yl)-ethoxy]-benzo[b]thiophen-7-yl}-acrylic acid methyl ester;

c) converting (Z)-2-methoxy-3-{4-[2-(5-methyl-2-phenyl-oxazol-4-yl)-ethoxy]-benzo[b]thiophen-7-yl}-acrylic acid methyl ester to (Z)-2-methoxy-3-{4-[2-(5-methyl-2-phenyl-oxazol-4-yl)-ethoxy]-benzo[b]thiophen-7-yl}-acrylic acid; and d) hydrogenating (Z)-2-methoxy-3-{4-[2-(5-methyl-2-phenyl-oxazol-4-yl)-ethoxy]-benzo[b]thiophen-7-yl}-acrylic acid using a procedure as defined in claim 1 to yield (S)-2-methoxy-3-{4-[2-(5-methyl-2-phenyl-oxazol-4-yl)-ethoxy]-benzo[b]thiophen-7-yl}-propionic acid.

* * * * *

UNITED STATES PATENT AND TRADEMARK OFFICE
CERTIFICATE OF CORRECTION

PATENT NO. : 7,262,303 B2  
APPLICATION NO. : 10/933176  
DATED : August 28, 2007  
INVENTOR(S) : Kurt Puentener et al.

Page 1 of 1

It is certified that error appears in the above-identified patent and that said Letters Patent is hereby corrected as shown below:

Title page, Item [73], delete "Hoffman-La Roche Inc.," and insert
-- Hoffmann-La Roche Inc., --

Signed and Sealed this

Tenth Day of June, 2008

JON W. DUDAS  
*Director of the United States Patent and Trademark Office*